(12) United States Patent
D'Abbene et al.

(10) Patent No.: US 11,574,364 B2
(45) Date of Patent: Feb. 7, 2023

(54) SYSTEMS AND METHODS FOR AUTOMATED REVIEW OF RISK ADJUSTMENT DATA ON SUBMITTED MEDICAL CLAIMS

(71) Applicant: Change Healthcare Holdings, LLC, Nashville, TN (US)

(72) Inventors: Colleen D'Abbene, Audubon, PA (US); William J. O'Neill, Cleveland, OH (US); Jimmy Liu, Cherry Hill, NJ (US); David Cardelle, Cohasset, MA (US)

(73) Assignee: Change Healthcare Holdings, LLC, Nashville, TN (US)

( * ) Notice: Subject to any disclaimer, the term of this patent is extended or adjusted under 35 U.S.C. 154(b) by 0 days.

(21) Appl. No.: 16/368,193

(22) Filed: Mar. 28, 2019

(65) Prior Publication Data
US 2020/0311823 A1    Oct. 1, 2020

(51) Int. Cl.
*G06Q 40/00* (2012.01)
*G06Q 40/08* (2012.01)
*G16H 50/70* (2018.01)

(52) U.S. Cl.
CPC ............. *G06Q 40/08* (2013.01); *G16H 50/70* (2018.01)

(58) Field of Classification Search
CPC ......... G16H 50/70; G06Q 40/08; G06Q 40/00
USPC ........................................................ 705/4
See application file for complete search history.

(56) References Cited

U.S. PATENT DOCUMENTS

| | | | |
|---|---|---|---|
| 7,725,330 B2* | 5/2010 | Rao ................... | G16H 10/60 705/3 |
| 7,979,289 B2 | 7/2011 | Callas | |
| 9,123,072 B2 | 9/2015 | Ketchell, III | |
| 2016/0055589 A1* | 2/2016 | Billings ............. | G06Q 40/08 705/4 |
| 2017/0039330 A1* | 2/2017 | Tanner, Jr. ......... | G06Q 10/00 |
| 2017/0364638 A1* | 12/2017 | Thesman ........... | G16H 10/60 |

FOREIGN PATENT DOCUMENTS

CN          1745390          3/2006

OTHER PUBLICATIONS

Google Scholar NPL (non-patent literature) Search Results, dated Nov. 20, 2021. (Year: 2021).*
Google Scholar Search, dated Jun. 7, 2022. (Year: 2022).*
Google Patents Search, dated Jun. 7, 2022. (Year: 2022).*

* cited by examiner

*Primary Examiner* — Hai Tran
(74) *Attorney, Agent, or Firm* — Meunier Carlin & Curfman LLC

(57) ABSTRACT

Disclosed and described herein are systems and methods of performing computer-aided analysis of health claims to determine if a current claim is consistent with past claims for a member. Consistent claims are directed to a healthcare payor while non-consistent claims are returned for review and/or revision.

18 Claims, 4 Drawing Sheets

SYSTEMS AND METHODS FOR AUTOMATED REVIEW OF RISK ADJUSTMENT DATA ON SUBMITTED MEDICAL CLAIMS

FIELD OF THE INVENTION

Embodiments of the present invention relate generally to systems and methods of applying, in real time at the time of submission, comparative and predictive analytics to the risk adjustment data on a submitted medical claim and on previously-submitted and archived medical claims for the same patient to identify actionable gaps in diagnosis coding.

BACKGROUND

Health plans participating in government sponsored programs including, for example, Medicare Advantage, Managed Medicaid, and the Commercial ACA market have an obligation to undertake due diligence to ensure the accuracy, completeness, and truthfulness of the risk adjustment data they submit to Centers for Medicare and Medicaid Services (CMS) or other healthcare payors (e.g., insurance companies, etc.). This data is primarily in the form of the diagnosis codes on medical claims. Conventionally, healthcare payors have relied on healthcare providers to code completely and accurately, but healthcare providers receive payment based on the codes that are submitted (including evaluation and management (E&M) (current procedural terminology (CPT) or procedure) codes), so there's a disconnect and not necessarily a shared objective between the healthcare provider and the healthcare payor. And while healthcare payors rely on healthcare providers to achieve their goals, healthcare providers are under continued pressures, with reduced fee schedules, programs from multiple payers, and programs are not typically aligned with healthcare provider workflows. Furthermore, because of the sheer volume of health claims generated by healthcare providers, it is impracticable if not impossible for healthcare payors to review, verify and confirm the diagnosis codes submitted by the healthcare providers to the healthcare payors in all health claims.

Traditionally, healthcare payors have relied on in-office chart reviews or requests for medical records so that they can be manually reviewed, which is burdensome to healthcare providers and costly to healthcare payors. Medical record reviews have other limitations as well. Some healthcare providers won't comply and won't provide the medical records. Sometimes the records can't be reviewed completely because of deadlines. Health plans may also be constrained by the cost of these reviews. The conventional approach can delay receiving reimbursement from healthcare payors up to 12 months for healthcare providers.

Healthcare payors, as an express condition of receiving payment or reimbursement from CMS, must certify, based on best knowledge, information, and belief, that their risk adjustment data they submit to CMS are accurate, complete, and truthful. CMS has made it clear that Medicare Advantage organizations have an obligation to undertake due diligence to ensure this, and that they are held responsible for making good faith efforts.

Therefore, a due diligence tool is desired that overcomes challenges in the art, some of which are described above, that better ensures accurate and complete coding by engaging healthcare providers within their existing billing workflow as the healthcare provider submits a claim.

BRIEF SUMMARY

Generally, disclosed and described herein are systems and methods that for performing computer-aided analysis of health claims, in real time at the time a claim is submitted, to determine if there are gaps in the diagnosis coding included within the current submitted claim, such that it is inconsistent with past claims for a member, or with what is expected for that member. Consistent claims, or claims that include expected diagnosis codes, are directed to a healthcare payor while non-consistent claims are returned for review and/or revision.

In one aspect, a method is disclosed for performing computer-aided analysis of an electronic health claim. One of the embodiments of the method comprises intercepting, by a computer, an electronic communication from a sender to a recipient, where the communication comprises at least a portion of a current electronic health claim associated with a member and the received portion of the current electronic health claim includes one or more diagnosis codes. The method further comprises identifying, by the computer, a set of one or more expected diagnosis codes, where the set of expected diagnosis codes are associated with a chronic disease or a chronic condition of the member. The computer determines whether at least one of the set of expected diagnosis codes is included in the one or more diagnosis codes of the current electronic health claim. If it is determined that at least one of the set of expected diagnosis codes is included in the one or more diagnosis codes of the current electronic health claim, the electronic communication is transmitted to the recipient. If it is determined that at least one of the set of expected diagnosis codes is not included in the one or more diagnosis codes of the current electronic health claim, a message is transmitted to the sender. The message identifies at least one of the expected diagnosis codes.

In various aspects of the disclosed methods, the sender is a healthcare provider and the recipient is a healthcare payor.

In some instances, the computer disclosed in the method comprises a clearinghouse and the clearinghouse is configured to communicate claim messages between the healthcare providers and the healthcare payors and, generally, the steps of the method are performed in real time upon submission of the electronic health claim to the clearinghouse.

Alternatively or optionally, identifying the set of expected diagnosis codes comprises accessing, by the computer, a database of health claims; identifying one or more prior chronic diagnosis codes included in one or more prior health claims for the member found in the database of health claims; determining, by the computer, a chronic disease or a chronic condition of the member as a chronic condition or chronic disease associated with the one or more prior diagnosis codes, wherein the chronic condition or chronic disease associated with the one or more prior diagnosis codes is determined by the computer accessing a database of mappings that maps diagnosis codes to chronic diseases or chronic conditions; and determining, by the computer, the set of expected chronic diagnosis codes as all chronic diagnosis codes associated with the chronic disease or chronic condition of the member as determined by the mapping of the one or more prior diagnosis codes of the member to the chronic disease or chronic condition associated with the one or more prior diagnosis codes using the database of mappings.

In some instances, the chronic disease or chronic condition of the member comprises one or more chronic diseases and/or one or more chronic conditions.

In some instances, when it is determined that at least one of the set of expected diagnosis codes is not included in the portion of the current electronic health claim, then the computer identifies at least one of the expected diagnosis codes to include in the message based on at least one of frequency of the chronic diagnosis codes found in the prior diagnosis codes or recency of chronic diagnosis codes found in the prior diagnosis codes.

Alternatively or optionally, when accessing the database of health claims, the computer only accesses and analyzes health claims associated with a defined period of time. For example, the defined time period may comprise three years prior to a date of the current electronic health claim.

Alternatively or optionally, identifying the set of expected diagnosis codes comprises the computer accessing a medical claim history of the member to determine a pattern that indicates existence of a potential chronic disease or chronic condition of the member, and identifying one or more chronic diagnosis codes associated with the potential chronic disease or chronic condition using a database of mappings that maps chronic diseases or chronic conditions to chronic diagnosis codes. The set of expected chronic diagnosis codes are the chronic diagnosis codes mapped to the potential chronic disease or chronic condition of the member. In some instances, the sender comprises a healthcare provider, and the computer further utilizes one or more of a specialty of the healthcare provider, what other healthcare providers in that specialty often diagnose, and/or an amount of time spent by the healthcare provider with the member when identifying the set of expected diagnosis codes.

In some instances, when it is determined that at least one of the set of expected diagnosis codes is not included in the one or more diagnosis codes of the current electronic health claim, and before transmitting the message to the sender, then a database of health claims is accessed by the computer, and the computer determines whether any prior health claim associated with the member over a past time period found in the database of health claims included a prior diagnosis code that is included in the set of expected diagnosis codes. If it is determined that at least one prior diagnosis code is included in the set of expected diagnosis codes, then the electronic communication is transmitted to the recipient and the message is not sent to the sender. If it is determined that at least one prior diagnosis code is not included in the set of expected diagnosis codes, then the message is sent to the sender. For example, the past time period may be one year prior to a date of the current electronic health claim.

Further disclosed and described herein are systems for implementing the methods disclosed herein.

Other objects and advantages will become apparent to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION

Figure 1A:
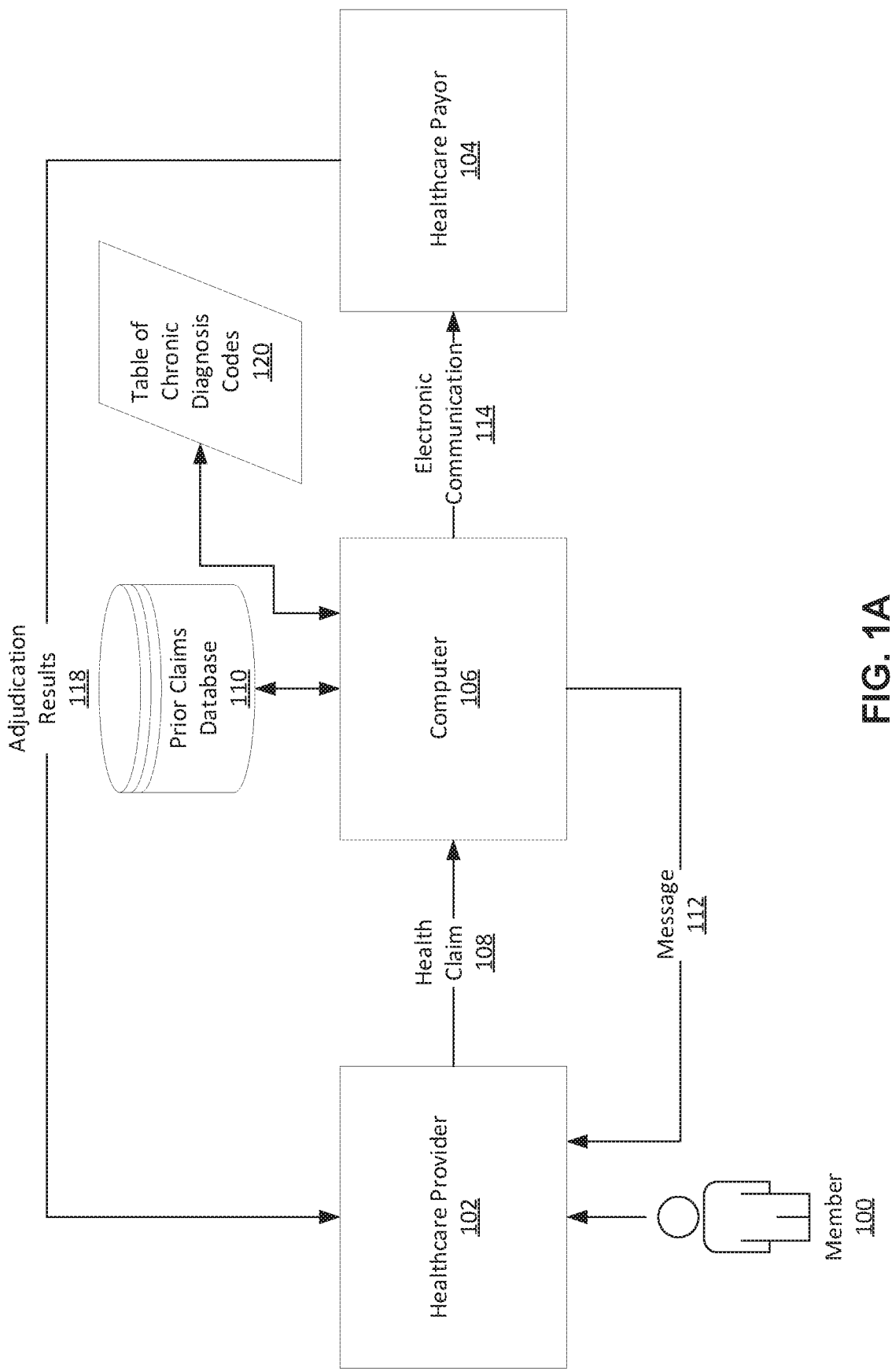
FIGS. 1A and 1B illustrate exemplary overview block diagrams of systems for performing aspects of the disclosed embodiments.

Before the present methods and systems are disclosed and described, it is to be understood that the methods and systems are not limited to specific synthetic methods, specific components, or to particular compositions. It is also to be understood that the terminology used in this entire application is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, to "about" another particular value, or from "about" one value to "about" another value. When such a range is expressed, another embodiment includes from the one particular value, to the other particular value, or from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

When referring to a diagnosis code that a provider includes on a health claim, the plural form of "codes" will be used for brevity but will have the same meaning as "one or more codes". In practice, a provider may associate more than one diagnosis codes to a health claim.

Use of the word "claim" follows the same style as "diagnosis code," as it is possible for multiple claims to be submitted, for example, to a healthcare payor (e.g., a primary and secondary insurer).

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, DVD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Additionally, the disclosed system, method and computer-program product can optionally be implemented within a cloud computing environment, for example, in order to decrease the time needed to perform the algorithms, which can facilitate processing of a health claim as software-as-a-service (SaaS). Cloud computing is well-known in the art. Cloud computing enables network access to a shared pool of configurable computing resources (e.g., networks, servers, storage, applications, and services) that can be provisioned and released with minimal interaction. It promotes high availability, on-demand self-services, broad network access, resource pooling and rapid elasticity. It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

The present methods and systems may be understood more readily by reference to the following detailed description of preferred embodiments and the Examples included therein and to the Figures and their previous and following description.

A. Overview

Described herein are embodiments of a system, method and computer program product (including SaaS) offering that provide targeted messages to healthcare providers based on identified gaps in the diagnosis coding included in health claims submitted by those providers. The disclosed embodiments screen health claims before submission to a health plan (i.e., healthcare payor) to generally identify health claims that do not include expected or anticipated chronic diagnosis codes. In one embodiment, this occurs upon receipt of the health claim by a clearinghouse, an intermediary that communicates claims information between healthcare providers to healthcare payors. When such claims are identified, they are returned to the submitter (e.g., healthcare provider) to provide an opportunity for medical record review and, if supported in the record, for claim editing.

More specifically, embodiments described herein identify the patient (i.e., member) and search for any chronic diagnosis codes previously documented for that member, each diagnosis code being associated with a disease category. Each chronic disease has a number of chronic diagnosis codes associated with it (e.g., disease A has diagnosis codes 1, 2 and 3 associated with it). If the patient's previous charts include chronic diagnosis codes 1 and 2, the embodiments described herein apply software analytics to look for any of diagnosis codes 1, 2 OR 3 in the current health claim—i.e., not just the specific diagnosis codes found in previous claims, but any diagnosis codes associated with that disease (disease A). For example, up to three (3) years of the prior claims for that member and any available medical record data may be searched to find prior submitted chronic diagnosis codes associated with one/more identified chronic diseases. If any chronic diagnosis codes are identified in the patient's history, embodiments described herein may first determine whether any claims submitted for that patient within the last year included a chronic diagnosis code associated with the same disease category as the previously submitted chronic diagnosis codes. If not, disclosed embodiments analyze the current health claim submitted to determine whether any such chronic diagnosis code is currently reported—i.e., a chronic diagnosis code that is associated with a chronic disease or disease category that has been identified in the patient's history. If a chronic diagnosis code associated with an identified chronic disease is not included on the current claim, and was not included in any claim submitted within the last year, a point-of-submission message is sent to the submitter identifying the health claim that requires review, and, for the healthcare provider's information only, the historically documented chronic diagnosis codes that were expected or anticipated to be present on the current health claim.

Figure 1B:
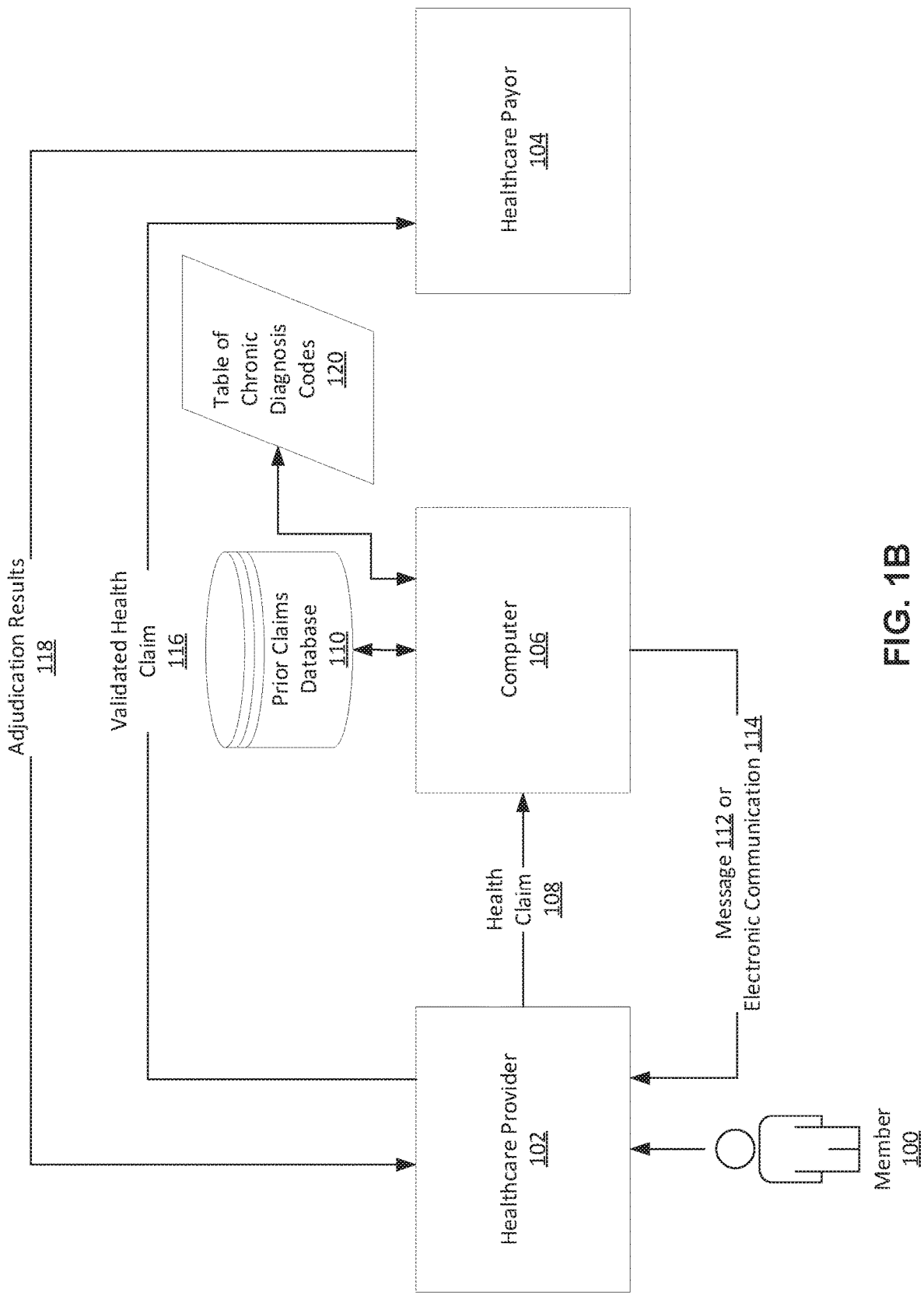

FIGS. 1A and 1B illustrate exemplary overview block diagrams of systems for performing aspects of the disclosed embodiments. In FIGS. 1A and 1B, an electronic health claim is created after a member 100 sees a healthcare provider 102. Generally, a "member" as used herein is a person that is properly enrolled and covered by a healthcare plan and is eligible for benefits including payment of or reimbursement for healthcare related costs by a healthcare payor 104. Generally, the payments will be sent from the healthcare payor 104 to the healthcare provider 102, though in some instances the payments may go directly from the healthcare payor 104 to the member 100 or in other instances, payments from the healthcare payor 104 to the healthcare provider 102 may be reimbursed by the healthcare provider 102 to the member 100. The healthcare provider 102 may be a doctor, a group of doctors, a physician's assistant, a nurse, a hospital, and the like. As used herein, "payments" include electronic communications of funds from one electronic account to another, a written check or other tangible representation of money such as money orders and the like, or cash transfers.

The electronic health claim is created by the healthcare provider 102 using a computer or computer system under control of the healthcare provider 102 (a "first computer"). The electronic health claim includes one or more diagnosis codes for the member as determined by the healthcare provider 102 who saw the member. As non-limiting examples, the diagnosis codes may be standardized codes such as the International Classification of Disease (ICD) codes (e.g., ICD-10) as published by the World Health Organization, though it is to be appreciated that other types of diagnosis codes may be used. In some instances, the electronic health claim may comprise an EDI 837 claims file in compliance with HIPAA (Health Insurance Portability and Accountability Act of 1996) requirements. The electronic health claim is used by the healthcare provider 102 to obtain payment from an insurance company, government entity or agency (CMS) or other paying entity (i.e., a "healthcare payor") 104 for the services and/or products used by the healthcare provider 102 when seeing and/or treating the member 100.

As shown in FIGS. 1A and 1B, a separate computer or computing system 106 (a "second computer") receives the electronic health claim 108, or at least a portion of the electronic health claim 108, at the point where the healthcare provider 102 submits the claim for payment. Because an electronic health claim 108 is generally transmitted from a healthcare provider 102 to a healthcare payor 104, the computer 106 may be said to "intercept" the electronic health claim 108 as it is transmitted from the healthcare provider 102 to the healthcare payor 104, though both the healthcare provider 102 and the healthcare payor 104 are aware of this interception and have agreed to it. Generally, the computer 106 comprises at least a processor and a memory in communication with the processor. Computer-executable instructions are stored on the memory and executed by the processor. The portion of the health claim 108 received includes at least the one or more diagnosis codes, information sufficient to identify the member that the diagnosis codes are associated with, and identification of the submitter. Generally, the health claim 108 or the portion of it is received by the computer 106 from the healthcare provider 102. In some instances, the computer 106 is operated by, for, and/or under the control of a health claim clearinghouse. In medical billing, companies that function as intermediaries who communicate claims information between healthcare providers and healthcare payors are known as clearinghouses. In what is called claims scrubbing, clearinghouses check health claims for errors.

In FIG. 1A, a healthcare provider 102 sees a member 100 and creates an electronic health claim 108, which is electronically transmitted to the computer 106. The health claim 108 contains information sufficient to identify the member 100, diagnosis codes associated with the member's 100 visit to the healthcare provider 102, information sufficient to identify the healthcare provider 102 that served the member 100 and submitted the health claim 108, and information sufficient to identify the healthcare payor 104 associated with the member 100. Once the health claim 108 is received by the computer 106, it is determined if the health claim 108 is associated with a member 100 covered by a healthcare plan for which the healthcare payor 104 wants the health claim 108 reviewed. If so, then information is extracted from the health claim 108 to find prior health claims submitted in association with that member. Various information from the health claim 108 may be used to look for prior health claims 108 for that member 100. For example, the health claim 108 may include an identifier (ID) for the insured (the insured may be the same person as the member 100 or may be a dependent or have another relationship with the member 100 such that the insured is covered by the member's 100 health plan (i.e., the patient)). The insured's identifier, the patient's date of birth (DOB), and all or portions of the patient's first and last name may be used in various combinations to search a database 110 of prior claims for information about prior claims submitted in association with the patient. If the health claim 108 received by the computer 106 is determined to be a health claim 108 that is not associated with a member 100 covered by a healthcare plan for which the healthcare payor 104 wants the health claim 108 reviewed, then the health claim 108 is returned to the sender (e.g., the healthcare provider 102), or is forwarded on to the healthcare payor 104, or is otherwise treated in accordance with rules established by the clearinghouse.

If information related to prior claims submitted in association with the patient is found in the database 110 of prior claims, then the prior diagnosis codes for that patient are determined from the database 110. Certain of all diagnosis codes are identified as chronic diagnosis codes, meaning that they are diagnosis codes associated with chronic diseases or conditions, where each chronic disease or condition may have more than one diagnosis code associated or mapped therewith. For example, the disease category of diabetes may have one chronic diagnosis code for "diabetes without complications" and another for "diabetes with complications." These chronic diagnosis codes may be developed according to regulatory risk adjustment models, which are primarily based on chronic conditions, though some acute conditions may also be included. The computer 106 has access to a table 120 that identifies chronic diagnosis codes (i.e., diagnosis codes associated with or mapped to specific chronic diseases or conditions). If at least some of the prior diagnosis codes for that patient that are retrieved from the database 110 are determined to be chronic diagnosis codes associated with at least one chronic disease, then the computer 106 of one embodiment first determines if any health claims 108 submitted for that member within the last predetermined period of time (e.g., one year) include a chronic diagnosis code associated with/mapped to that chronic disease. If not, the computer 106 further determines if the current health claim 108 includes a chronic diagnosis code associated with/mapped to the previously reported chronic disease or disease category. As noted herein, the health claim 108 is generally a formatted electronic communication (e.g. an EDI 837 claims file), where the diagnosis codes are formatted and identified in the health claim 108, thus making them readily identifiable in the health claim 108.

If none of the chronic diagnosis codes associated with/mapped to an identified chronic disease for that patient are found on the current health claim 108, then a message 112 is electronically transmitted to the sender (e.g. healthcare provider 102) that submitted the current health claim 108. In some instances, the message 112 identifies chronic diagnosis codes that were expected or anticipated to be present in the current health claim 108 based on the prior health claims associated with that patient that are found in the database 110. In some instances, only a few of the chronic diagnosis codes that were expected or anticipated to be present in the current health claim 108 are included in the message 112. Also, in some instances, only a predetermined time period is used to look for prior chronic diagnosis codes associated with a patient in reverse chronological order in the database 110. For example, five chronic diagnosis codes may be found in the database 110 associated with the patient in a search of the database 110 that extends to a three-year look-back. If none of these five prior chronic diagnosis codes are included in the current health claim 108, then perhaps only a subset of the five found prior chronic diagnosis codes will be included in the message 112. The subset of chronic diagnosis codes selected to return in the message 112 may be based on recency, frequency, severity of the disease associated with the chronic diagnosis code(s), etc. In some instances, the subset comprises two expected chronic diagnosis codes, though more or fewer numbers of expected chronic diagnosis codes may be included in the message.

The message 112 may also include a request for the healthcare provider 102 to review and resubmit the health claim 108. If the healthcare provider 102 resubmits the health claim 108, it will be identified as a re-submission and the re-submitted diagnosis codes will be reviewed by the computer 106 to determine if they are chronic diagnosis codes that were previously associated with that patient in the database 110, if the current diagnosis codes associated with the health claim 108 are associated with chronic diagnosis codes that have not been previously associated with that patient in the database 110, if they are the same chronic diagnosis codes as were suggested to the healthcare provider 102 in the message, and/or if they are the same diagnosis codes as were previously submitted in the earlier-submitted health claim 108.

If the re-submitted diagnosis codes are chronic diagnosis codes that were previously associated with that patient in the database 110, then the health claim 108 is marked as having been checked for errors and is electronically transmitted as an electronic communication 114 to the healthcare payor 104. If the re-submitted diagnosis codes associated with the health claim 108 are associated with chronic diagnosis codes that have not been previously associated with that patient in the database 110, but are found in the table 120 of chronic diagnosis codes, then the health claim 108 is marked as having been checked for errors and is electronically transmitted to the healthcare payor 104 as an electronic communication 114. If the re-submitted diagnosis codes are the same chronic diagnosis codes as were previously suggested in the message 112 back to the healthcare provider 102, then this is noted and stored in a memory associated with the computer 106 (this may be stored in the database 110 or in other memory), and the health claim 108 is marked as having been checked for errors and is electronically transmitted to the healthcare payor 104 as an electronic communication 114. If the re-submitted health claim 108 still does not include any chronic diagnosis codes that have been previously associated with the patient (as determined by a search of the database 110) but does include a diagnosis code that is found in the table 120 of chronic diagnosis codes, then this is noted and stored in a memory associated with the computer 106 (this may be stored in the database 110 or in other memory). The health claim 108 is then passed on to the healthcare payor 104 in an electronic communication 114, but the electronic communication 114 may include a message that the re-submitted health claim 108 includes a chronic diagnosis code, but does not include any chronic diagnosis codes that have been previously associated with the patient.

The message 112 transmitted to the healthcare provider 102 creates an obligation for the healthcare provider 102 to review the medical record of the patient and to ensure that, to the best of the healthcare provider's 102 knowledge, information and belief, the submitted claims are accurate, complete and truthful. The subset of chronic diagnosis codes selected to return in the message offers assurance to health care providers 102 that diagnosis codes are not overlooked in the health claim 108 and makes chart review more efficient.

In some instances, the message 112 to the healthcare provider 102 and/or the electronic communication 114 to the healthcare payor 104 comprises all or a part of an ANSI X12 EDI 277 CA (claims acknowledgment) transaction. The EDI 277 Health Care Claim Status Response transaction set is used by healthcare payers (insurance companies, Medicare, etc.) to report on the status of claims (837 transactions) previously submitted by providers. The 277 transaction has been specified by HIPAA for the submission of claim status information. In some instances, the expected chronic diagnosis codes are returned in a text field of the EDI 277CA communication.

In some instances (see FIG. 1B), an electronic communication 114 may be electronically transmitted to the healthcare provider 102 with an explanation of the review of the health claim 108 performed by the computer 106. In some instances the electronic communication 114 includes an indication that the current electronic health claim is valid and the healthcare provider 102 in turn submits the validated health claim 116 directly to the healthcare payor 104. For example, the current electronic health claim may be indicated as being validated by using an electronic indicator, a syntactical code, and the like that define that the health claim was "accepted" and submitted to the healthcare payor 104 for adjudication. Alternatively, or optionally, the electronic communication 114 may be electronically transmitted to the healthcare payor 104 with an indication that the current health claim 108 is valid and for the healthcare payor 104 to adjudicate 118 the electronic health claim 108. Such adjudication may include payment of all or a portion of the amount associated with the health claim 108.

In other instances (not shown in FIG. 1A or 1B) an electronic communication 114 may be electronically transmitted to the healthcare payor 104 with an explanation of the analysis of the health claim 108 performed by the computer 106 and/or a request to review and re-submit the current electronic health claim 108. The healthcare payor 104 would then contact the healthcare provider 102 with a request to review and re-submit the current electronic health claim 108. As with the above, the e electronic communication transmitted to the healthcare payor 104 may also include the one or more expected or anticipated chronic diagnosis codes that were missing from the original health claim 108 submission. Such an electronic communication 114 to the healthcare payor 104 pay be done with a message 112 of the same information to the healthcare provider 102, or alone without a message 112 to the healthcare provider 102.

According to yet another embodiment, the computer 106, using machine learning and other predictive analytics tools, identifies one or more chronic diagnosis codes that likely should have been included within the current health claim 108 but where not. For example, the computer 106 may access the member's medical claim history, which includes information on tests run, lab results received, medications prescribed, and the like, to look for patterns of behavior that indicate the likely existence of a chronic disease. Where a pattern is identified, and the current health claim 108 does not include a diagnosis code associated with that chronic disease, a message 112 may be communication to the healthcare provider 102, even though the prior health claims 108 associated with the member similarly do not include diagnosis codes associated with that chronic disease. Other factors associated with the healthcare provider 102 may also be taken into consideration when predicting that a chronic diagnosis code is likely missing from a health claim 108. For example, embodiments may take into consideration the specialty of the healthcare provider 102 and what other providers in that specialty often diagnosis, the time spent with the member 100, and/or the like.

In the exemplary systems shown in FIGS. 1A and 1B, health claims 108, messages 112 and electronic communications 114 may be received, processed and payments transmitted or authorized using a computer or computer system under the control of the healthcare payor 104 (a "third computer"). Electronic communications between the first, second and/or third computer occur using networks (wired (including fiber optic), wireless, or combinations of wired and wireless). For example, at least a portion of the network may comprise the internet and/or a virtual private network (VPN) using the internet.

If the database 110 of prior health claims is searched and no prior claim is found that is associated with the member 100, then at least the one or more diagnosis codes of the current health claim 108 can be associated with the member and stored in the database 110 along with information identifying the member 100, the submitting healthcare provider 102, and the healthcare plan to which that member 100 belongs. In some instances the diagnosis codes stored in the database 110 are chronic diagnosis codes, as described herein. In some instances, the current diagnosis codes may not be associated with a chronic disease or condition, as determined by a search of the table 120 of chronic diagnosis codes by the computer 106. Generally, in such an instance, the diagnosis codes of the current health claim 108 are not stored in the database 110. An electronic message can be electronically transmitted to one or both of the healthcare provider 102 or the healthcare payor 104 that no prior claims associated with the member were found and/or none of the current diagnosis codes are found in the table 120 of chronic diagnosis codes.

B. Auditing

As noted herein, the computer 106 tracks health claim 108 submissions, messages 112, and electronic communications 114. The computer 106 may track whether a specific healthcare provider 102 or healthcare payor 104 submits health claims 108 that are missing chronic diagnosis codes and/or have incorrect diagnosis codes. The computer 106 may also track whether a specific healthcare provider 102 or healthcare payor 104 re-submits health claims 108 upon receiving a message 112 that suggests expected chronic diagnosis codes, where the re-submitted chronic diagnosis codes are comprised of the chronic diagnosis codes that were suggested to the healthcare provider 102. The computer 106 may also track whether a specific healthcare provider 102 re-submits health claims 108 upon receiving a message 112 that expected chronic diagnosis codes are missing and the re-submitted diagnosis codes are consistently comprised of a small set of the same chronic diagnosis codes used over and over for different patients. The computer 106 may also track whether a specific healthcare provider 102 has a higher incidence rate than an average of some other healthcare providers 102 of submitting health claims 108 that are missing chronic diagnosis codes and/or have incorrect diagnosis codes. These are only non-limiting examples of the analytics that can be performed by the computer 106 in tracking health claim 108 submissions, messages 112, and electronic communications 114, and the information included with the messages 112 and/or electronic communications 114. These analytics can be used to trigger audits of the offending healthcare providers' 102 and/or healthcare payors' 104 practices and procedures in creating, submitting and managing health claims 108. Such analytics can be used to detect insurance fraud or just careless (and inefficient) practices and procedures.

C. Processes and Methods

Figure 2:
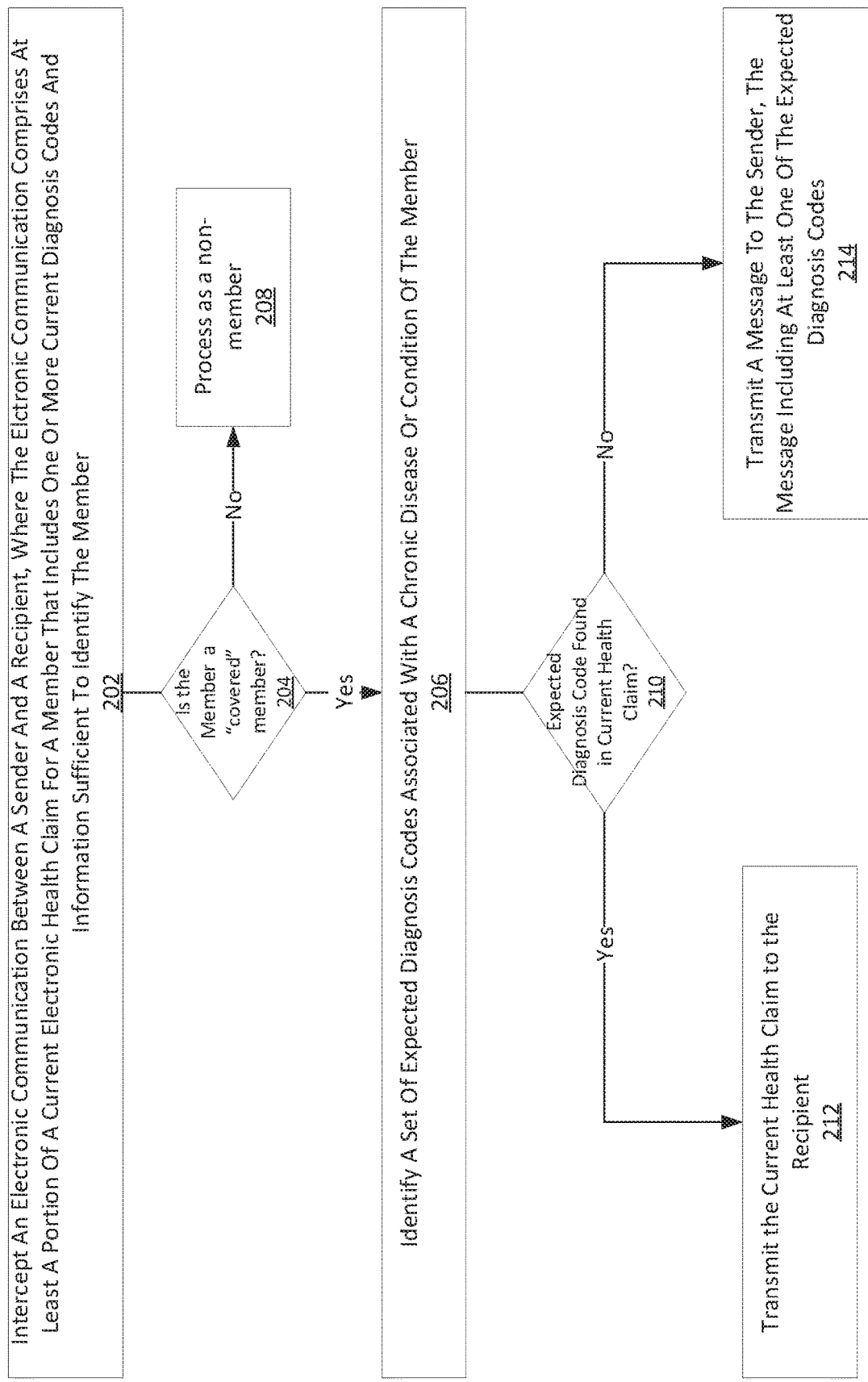
FIG. 2 is a flowchart illustrating an example of a process for performing computer-aided analysis of an electronic health claim.

FIG. 2 is a flowchart illustrating an example of a process for performing computer-aided analysis of an electronic health claim. At 202, at least a portion of a current electronic health claim for a member sent as an electronic communication between a sender and a receiver is intercepted by a computer. The intercepted and received portion of the current electronic health claim includes one or more current diagnosis codes, information sufficient to identify the associated member, and information to identify the sender and the recipient. At 204, a determination is made if the member is associated with a healthcare plan (e.g., healthcare payor) that desires a review of chronic conditions of the member. If, at 204, a determination is made that the member is not associated with a healthcare plan (e.g., healthcare payor) that desires a review of chronic conditions of the member, then at 208 the health claim is treated in accordance with non-member rules, which may include returning the health claim to the sender, forwarding it on to the recipient (e.g., a healthcare payor, without any additional analysis of the health claim), or simply ignoring the health claim.

If, at 204, it is determined that the member is associated with a healthcare plan that desires a review of chronic conditions of the member, then at 206 the computer identifies a set of one or more expected diagnosis codes that are associated with a chronic disease or condition of the member. In one embodiment, this is done using a database of health claims that is analyzed by the computer to identify a set of one or more expected diagnosis codes, where the set of expected diagnosis codes are associated with a chronic disease or a chronic condition of the member. In particular, each of the one or more prior health claims stored in the database of health claims that are associated with the member include one or more prior diagnosis codes associated with the member. The database of health claims includes identifying information for a plurality of members and the one or more prior diagnosis codes associated with prior health claims of each of the plurality of members. The database is created from information received from a plurality of healthcare providers and/or a plurality of healthcare payors. The diagnosis codes stored in the database of health claims include chronic diagnosis codes associated with and mapped to chronic diseases and/or conditions of the member.

In one embodiment, in order to identify the set of one or more expected diagnosis codes, the computer first analyzes the prior health claims of the member to identify the prior diagnosis codes included within those prior health claims. The computer may then determine one or more chronic diseases or conditions associated with/mapped to the identified prior diagnosis codes and, therefore, associated with the member. Finally, the computer may identify the full set of diagnosis codes associated with that chronic disease(s) or condition(s) as the set of expected diagnosis codes.

In other instances, the computer identifies the set of one or more expected diagnosis codes that likely should have been included within the current health claim by, for example, the computer accessing the member's medical claim history, which includes information on tests run, lab results received, medications prescribed, and the like, to look for patterns of behavior that indicate the likely existence of a chronic disease, and then identifying as the set of expected diagnosis codes the full set of diagnosis codes associated with that chronic disease.

Other factors associated with the healthcare provider may also be taken into consideration by the computer when identifying the set of one or more expected diagnosis codes. For example, consideration may be given by the computer as to the specialty (oncologist, etc.) of the sender and what other providers in that specialty often diagnose, the time spent with the member, and/or the like.

At 210 it is determined, by the computer, whether or not at least one of the set of expected diagnosis codes is included in the one or more diagnosis codes of the current electronic health claim. If, at 210, it is determined that at least one of the set of expected diagnosis codes is included, then the process goes to 212. At 212, the computer transmits the electronic communication to the recipient. Generally, this comprises an electronic transmission to a healthcare payor with an indication for the healthcare payor to adjudicate the electronic health claim. At 214, when it is determined at 210 that at least one of the set of expected diagnosis codes is not included in the current electronic health claim, a message is transmitted to the sender. The message identifies at least one of the expected diagnosis codes.

In some instances, the computer determining whether at least one of the set of expected diagnosis codes is included in the current health claim comprises confirming whether at least one of the current diagnosis codes corresponds to a chronic disease for which one or more diagnosis codes were found in prior claims for the member. Alternatively, where the set of expected diagnosis codes was determined based on an identified pattern, and the current health claim does not include a diagnosis code associated with that chronic disease, a message may be communicated to the sender identifying at least some of the expected chronic diagnosis codes, even though the prior health claims associated with the member similarly do not include diagnosis codes associated with that chronic disease.

In some instances, the message transmitted to the sender includes, along with the at least one expected chronic diagnosis code, an explanation of the reason the health claim is being returned, and/or a request to review and re-submit the current electronic health claim.

In some instances, when it is determined by the computer that at least one of the set of expected diagnosis codes is included in the portion of the electronic health claim, then the electronic communication is transmitted by the computer back to the sender (rather than to the recipient). In such instances, an indication can be provided that the current electronic health claim is valid, and the healthcare provider submits the validated health claim directly to the recipient (e.g., healthcare payor). For example, the current electronic health claim may be indicated as being validated by using an electronic indicator, a syntactical code, and the like that define that the health claim was "accepted" and can be submitted to the healthcare payor for adjudication.

In instances where the healthcare provider received a message indicating that expected diagnosis codes are missing, the healthcare provider may re-submit the health claim. Such a resubmission may have an indicator that it is a re-submitted health claim, as described herein.

D. Computing Environment

Figure 3:
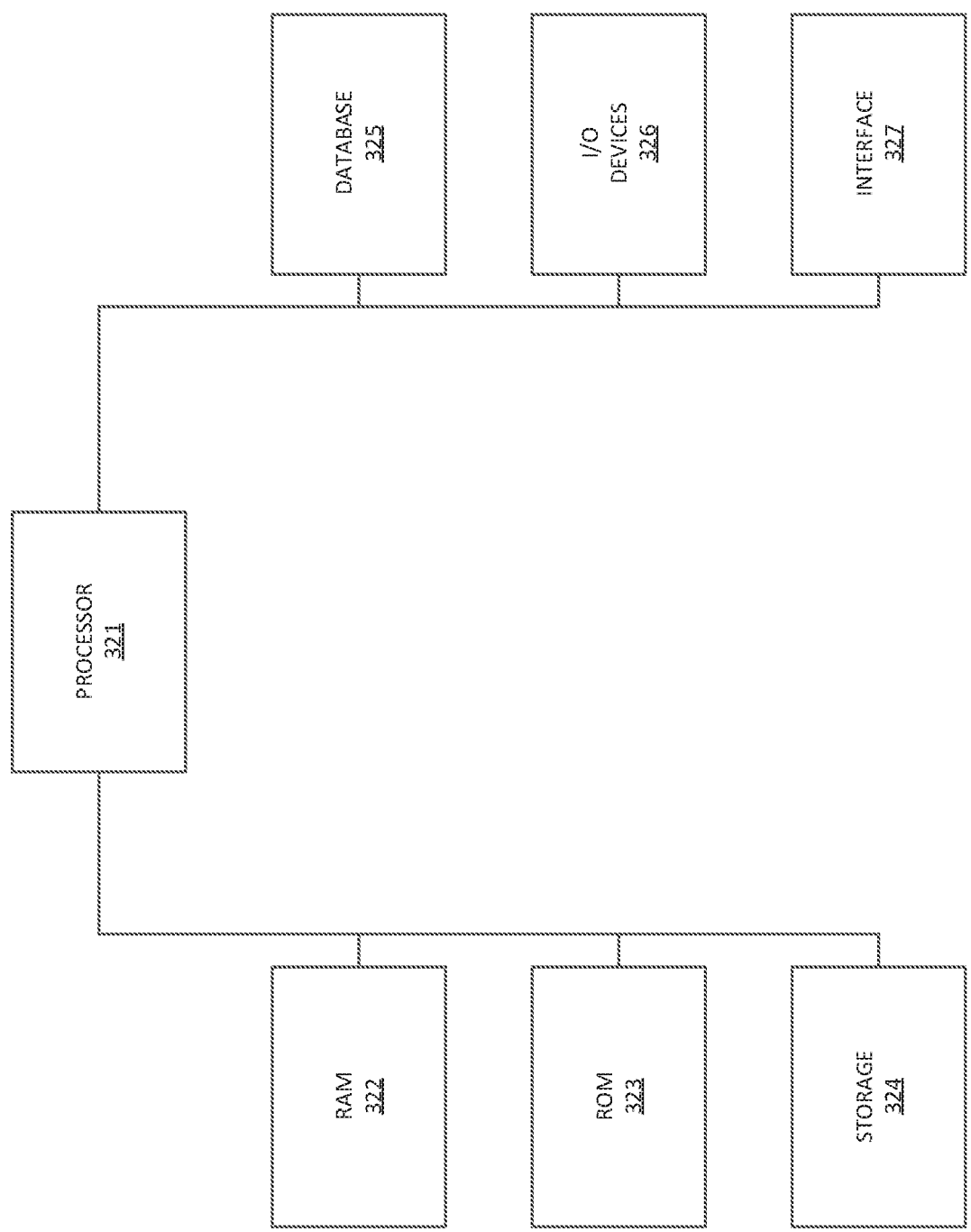
FIG. 3 illustrates an exemplary computer or computing device that can be used for some, a portion of, or all of the set of features and components described herein.

FIG. 3 illustrates an exemplary computer or computing device that can be used for some, a portion of, or all of the features and/or components described herein. All or a portion of the device shown in FIG. 3 may comprise all or any portion of any of the components and devices described herein that may include and/or require a processor or processing capabilities such as the first computer, the second computer, the third computer, etc. As used herein, "computer" may include a plurality of computers. The computers may include one or more hardware components such as, for example, a processor 321, a random-access memory (RAM) module 322, a read-only memory (ROM) module 323, a storage 324, a database 325, one or more input/output (I/O) devices 326, and an interface 327. Alternatively, and/or additionally, the computer may include one or more software components such as, for example, a computer-readable medium including computer executable instructions for performing a method or methods associated with the exemplary embodiments. It is contemplated that one or more of the hardware components listed above may be implemented using software. For example, storage 324 may include a software partition associated with one or more other hardware components. It is understood that the components listed above are exemplary only and not intended to be limiting.

Processor 321 may include one or more processors, each configured to execute instructions and process data to perform one or more functions associated with a computer for performing computer-aided analysis of an electronic health claim. Processor 321 may be communicatively coupled to RAM 322, ROM 323, storage 324, database 325, I/O devices 326, and interface 327. Processor 321 may be configured to execute sequences of computer program instructions to perform various processes. The computer program instructions may be loaded into RAM 322 for execution by processor 321.

RAM 322 and ROM 323 may each include one or more devices for storing information associated with operation of processor 321. For example, ROM 323 may include a memory device configured to access and store information associated with the computer, including information for identifying, initializing, and monitoring the operation of one or more components and subsystems. RAM 322 may include a memory device for storing data associated with one or more operations of processor 321. For example, ROM 323 may load instructions into RAM 322 for execution by processor 321.

Storage 324 may include any type of mass storage device configured to store information that processor 321 may need to perform processes corresponding with the disclosed embodiments. For example, storage 324 may include one or more magnetic and/or optical disk devices, such as hard drives, CD-ROMs, DVD-ROMs, or any other type of mass media device.

Database 325 may include one or more software and/or hardware components that cooperate to store, organize, sort, filter, and/or arrange data used by the computer and/or processor 321. For example, database 325 may store information and instructions related to prior health claims made by a member including information sufficient to identify the member and diagnosis codes associated with the health claim (and the member). It is contemplated that database 325 may store additional and/or different information than that listed above.

I/O devices 326 may include one or more components configured to communicate information with a user associated with computer. For example, I/O devices may include a console with an integrated keyboard and mouse to allow a user to maintain the database of prior health claims, and the like. I/O devices 326 may also include a display including a graphical user interface (GUI) for outputting information on a monitor. I/O devices 326 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 327 may include one or more components configured to transmit and receive data via a communication network, such as the Internet, a local area network, a workstation peer-to-peer network, a direct link network, a wireless network, or any other suitable communication platform. For example, interface 327 may include one or more modulators, demodulators, multiplexers, demultiplexers, network communication devices, wireless devices, antennas, modems, and any other type of device configured to enable data communication via a communication network.

As noted herein, the computer or computing device illustrated in FIG. 3 may comprise all or a part of a cloud computing environment.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for performing computer-aided analysis and certification of risk adjustment data associated with an electronic health claim submitted to a Center for Medicare and Medicaid Services (CMS) to certify that the risk adjustment data is accurate, complete, and truthful, said method comprising:

intercepting, by a computer, an electronic communication transmitted from a sender to a recipient, the electronic communication comprising at least a portion of a current electronic health claim associated with a member, said portion of the current electronic health claim associated with the member including one or more diagnosis codes associated with the member and an identifier for the member;

determining, by the computer, whether the member is covered by a health care plan provided by the recipient by querying a database of prior electronic health claims using the identifier, wherein the database comprises information from a plurality of healthcare providers and/or a plurality of healthcare payors;

identifying, by the computer and responsive to determining that the member is covered by the health care plan, a set of expected diagnosis codes for the current electronic health claim by querying an electronic medical history of the member stored in the database, said set of expected diagnosis codes associated with a chronic disease or a chronic condition of the member and identified by:

querying the electronic medical history for previously submitted diagnosis codes associated with the member, and responsive to identifying at least one previously submitted diagnosis code, determining a chronic condition associated with the at least one previously submitted diagnosis code, wherein the set of expected diagnosis codes are mapped to the chronic condition in the database;

determining, by the computer, whether at least one of the set of expected diagnosis codes is included in the one or more diagnosis codes of the current electronic health claim;

when it is determined that at least one of the set of expected diagnosis codes is included in the one or more diagnosis codes of the current electronic health claim, transmitting the electronic communication to a recipient computer of the recipient, wherein the recipient certifies the risk adjustment data associated with the electronic health claim is accurate, complete and truthful based on the determination that at least one of the set of expected diagnosis codes is included in the one or more diagnosis codes of the current electronic health claim and said recipient submits the certified electronic health claim to the CMS for reimbursement; and when it is determined that at least one of the set of expected diagnosis codes is not included in the one or more diagnosis codes of the current electronic health claim, then:

not sending the electronic communication to the recipient computer of the recipient, transmitting a message to the sender computer of the sender, said message identifying the expected diagnosis codes, and tracking an incident rate for the sender by updating the database to include an indication that the current electronic health claim was missing the at least one of the set of expected diagnosis codes, wherein the incident rate for the sender is compared to incident rates of other healthcare providers to trigger an audit of the sender's practices and procedures.

2. The method of claim 1, wherein the sender is a healthcare provider and the recipient is a healthcare payor.

3. The method of claim 2, wherein the computer comprises a clearinghouse and the clearinghouse is configured to communicate claim messages between healthcare providers and healthcare payors.

4. The method of claim 1, wherein when it is determined that at least one of the set of expected diagnosis codes is not included in the portion of the current electronic health claim, then the method further comprises the computer identifying at least one of the expected diagnosis codes to include in the message based on at least one of frequency of the chronic diagnosis codes found in the prior diagnosis codes or recency of chronic diagnosis codes found in the prior diagnosis codes.

5. The method of claim 1, wherein when accessing, by the computer, the database of health claims, the computer only accesses and analyzes health claims associated with a defined period of time.

6. The method of claim 1, wherein identifying the set of expected diagnosis codes comprises:

querying, by the computer, the electronic medical history of the member to determine a pattern that indicates existence of a potential chronic disease or chronic condition of the member; and identifying, by the computer, one or more chronic diagnosis codes associated with the potential chronic disease or chronic condition using the database which includes mappings of chronic diseases or chronic conditions to chronic diagnosis codes.

7. The method of claim 6, wherein the sender comprises a healthcare provider, and wherein the computer further utilizes one or more of a specialty of the healthcare provider, what other healthcare providers in that specialty often diagnose, and/or an amount of time spent by the healthcare provider with the member when identifying the set of expected diagnosis codes.

8. The method of claim 1, wherein when it is determined that at least one of the set of expected diagnosis codes is not included in the one or more diagnosis codes of the current electronic health claim, and before transmitting the message to the sender, then:

accessing, by the computer, the electronic medical history of the member;

determining, by the computer, whether any prior health claim associated with the member over a past time period found in the database of health claims include at least one of the previously submitted diagnosis codes that are included in the set of expected diagnosis codes;

when it is determined, by the computer, that at least one prior diagnosis code is included in the set of expected diagnosis codes, then transmitting the electronic communication to the recipient computer of the recipient and not sending the message to the sender computer of the sender; and when it is determined, by the computer, that at least one prior diagnosis code is not included in the set of expected diagnosis codes, then sending the message to the sender computer of the sender.

9. The method of claim 1, wherein when it is determined that at least one of the set of expected diagnosis codes is not included in the one or more diagnosis codes of the current electronic health claim, then: the computer accessing, by the computer, the electronic medical history of the user to identify past health claims associated with the member and the previously submitted diagnosis codes associated with the past health claims; and determining the set of expected diagnosis codes to include in the message based on at least one of frequency of chronic diagnosis codes found in the previously submitted diagnosis codes, or recency of chronic diagnosis codes found in the previously submitted diagnosis codes.

10. A system for performing computer-aided analysis and certification of risk adjustment data associated with an electronic health claim submitted to a Center for Medicare and Medicaid Services (CMS) to certify that the risk adjustment data is accurate, complete, and truthful, the system comprising:

a computer comprising at least a processor and a memory, wherein the memory is in communication with the processor, and wherein computer-executable instructions are stored on the memory and executed by the processor, said computer-executable instructions causing the processor to:

intercept an electronic communication from a sender computer to a recipient computer, wherein the electronic communication includes a current electronic health claim associated with a member, the electronic health claim including one or more diagnosis codes associated with the member and an identifier for the member;

determine whether the member is covered by a health care plan provided by a healthcare payor that operates the recipient computer by querying a database of prior electronic health claims using the identifier, wherein the database comprises information from a plurality of healthcare providers and/or a plurality of healthcare payors including the healthcare payor that operates the recipient computer;

responsive to determining that the member is covered by the health care plan, predict a set of one or more expected diagnosis codes for the current electronic health claim by querying an electronic medical history of the member stored in the database, said set of expected diagnosis codes associated with a chronic disease or a chronic condition of the member and identified by:

querying the electronic medical history for previously submitted diagnosis codes associated with the member, and responsive to identifying at least one previously submitted diagnosis code, determining a chronic condition associated with the at least one previously submitted diagnosis code, wherein the set of expected diagnosis codes are mapped to the chronic condition in the database;

determine whether at least one of the set of expected diagnosis codes is included in the one or more diagnosis codes of the current electronic health claim;

when it is determined that at least one of the set of expected diagnosis codes is included in the one or more diagnosis codes of the current electronic health claim, transmit the electronic communication to the recipient computer, wherein the recipient certifies the risk adjustment data associated with the electronic health claim is accurate, complete and truthful based on the determination that at least one of the set of expected diagnosis codes is included in the one or more diagnosis codes of the current electronic health claim and said recipient submits the certified electronic health claim to the CMS for reimbursement; and when it is determined that at least one of the set of expected diagnosis codes is not included in the one or more diagnosis codes of the current electronic health claim, then:

not sending the electronic communication to the recipient computer, transmitting a message to the sender computer, said message identifying at least one of the expected diagnosis codes, and tracking an incident rate for a healthcare provider that operates the sender computer by updating the database to include an indication that the current electronic health claim was missing the at least one of the set of expected diagnosis codes, wherein the incident rate for the healthcare provider that operates the sender computer is compared to incident rates of other ones of the plurality of healthcare providers healthcare providers to trigger an audit of the healthcare provider's practices and procedures.

11. The system of claim 10, wherein the sender computer is associated with a healthcare provider and the recipient computer is associated with a healthcare payor.

12. The system of claim 11, wherein the computer comprises a clearinghouse and the clearinghouse is configured to communicate claim messages between healthcare providers and healthcare payors.

13. The system of claim 10, wherein when it is determined that at least one of the set of expected diagnosis codes is not included in the portion of the current electronic health claim, then the method further comprises the computer identifying at least one of the expected diagnosis codes to include in the message based on at least one of frequency of the chronic diagnosis codes found in the prior diagnosis codes or recency of chronic diagnosis codes found in the prior diagnosis codes.

14. The system of claim 13, wherein when accessing, by the computer, the database of health claims, the computer only accesses and analyzes health claims associated with a defined period of time.

15. The system of claim 10, wherein identifying the set of expected diagnosis codes comprises the computer executing computer-executable instruction to:

access a medical claim history of the member to determine a pattern that indicates existence of a potential chronic disease or chronic condition of the member; and identify one or more chronic diagnosis codes associated with the potential chronic disease or chronic condition using the database which includes mappings of chronic diseases or chronic conditions to chronic diagnosis codes.

16. The system of claim 15, wherein the sender computer is associated with a healthcare provider, and wherein the computer further executes computer-executable instructions to utilize one or more of a specialty of the healthcare provider, what other healthcare providers in that specialty often diagnose, and/or an amount of time spent by the healthcare provider with the member when identifying the set of expected diagnosis codes.

17. The system of claim 10, wherein when it is determined that at least one of the set of expected diagnosis codes is not included in the one or more diagnosis codes of the current electronic health claim, and before transmitting the message to the sender computer, then the computer executes computer-executable instructions to:

access the electronic medical history of the member;

determine whether any prior health claim associated with the member over a past time period found in the database of health claims include at least one of the previously submitted diagnosis code that is included in the set of expected diagnosis codes;

when it is determined that at least one prior diagnosis code is included in the set of expected diagnosis codes, then transmitting the electronic communication to the recipient computer and not sending the message to the sender computer; and when it is determined that at least one prior diagnosis code is not included in the set of expected diagnosis codes, then sending the message to the sender computer.

18. The system of claim 11, wherein when it is determined that at least one of the set of expected diagnosis codes is not included in the one or more diagnosis codes of the current electronic health claim, then the computer executes computer-executable instructions to:

access the electronic medical history of the user to identify past health claims associated with the member and the previously submitted diagnosis codes associated with the past health claims associated with the member; and determine the set of expected diagnosis codes to include in the message based on at least one of frequency of chronic diagnosis codes found in the previously submitted diagnosis codes, or recency of chronic diagnosis codes found in the previously submitted diagnosis codes.

* * * * *